United States Patent [19]

Geithman et al.

[11] Patent Number: 4,700,575

[45] Date of Patent: Oct. 20, 1987

[54] ULTRASONIC TRANSDUCER WITH SHAPED BEAM INTENSITY PROFILE

[75] Inventors: Glenn A. Geithman; Dennis H. Gilbert, both of Renton, Wash.

[73] Assignee: The Boeing Company, Seattle, Wash.

[21] Appl. No.: 815,162

[22] Filed: Dec. 31, 1985

[51] Int. Cl.⁴ ............................................. G01N 29/00
[52] U.S. Cl. ........................................ 73/642; 73/644; 310/326
[58] Field of Search .................... 73/642, 644; 310/326

[56] References Cited

U.S. PATENT DOCUMENTS

| | | |
|---|---|---|
| 2,430,013 | 11/1947 | Hansell . |
| 2,477,246 | 7/1949 | Gillespie . |
| 2,481,068 | 9/1949 | Best . |
| 3,663,842 | 5/1972 | Miller ................................ 73/642 |
| 3,687,219 | 8/1972 | Langlois . |
| 3,958,559 | 5/1976 | Glenn et al. ........................ 73/642 |
| 4,144,508 | 3/1979 | Lewis et al. . |
| 4,205,686 | 6/1980 | Harris et al. ........................ 73/644 |
| 4,284,094 | 8/1981 | Behrend . |
| 4,557,146 | 12/1985 | Buffington et al. .................. 73/642 |
| 4,558,598 | 12/1985 | Young ................................ 73/644 |
| 4,616,152 | 10/1986 | Saito et al. ........................ 310/327 |

Primary Examiner—Howard A. Birmiel
Attorney, Agent, or Firm—Finnegan, Henderson, Farabow, Garrett & Dunner

[57] ABSTRACT

An ultrasonic transducer for generating an apodized beam of ultrasonic energy. A piezoelectric crystal element mounted in a housing generates on ultrasonic signal when electrically energized. A tungsten-epoxy layer mounted on the outer surface of the piezoelectric crystal element has a greater thickness at the periphery of the element than at the center, thus yielding an outwardly concave surface. The tungsten-epoxy layer provides a more uniform beam pattern.

17 Claims, 5 Drawing Figures

TTU BEAM PATTERN OF STANDARD 1/5 MHz TRANSDUCER DRIVEN @ 5 MHz

TTU BEAM PATTERN OF APODIZED 1/5 MHZ TRANSDUCER DRIVEN @ 5 MHZ

ULTRASONIC TRANSDUCER WITH SHAPED BEAM INTENSITY PROFILE

CROSS REFERENCE TO RELATED APPLICATIONS

The invention is related to the following copending U.S. patent applications assigned to the assignee of the present invention:

DATA RECORDING APPARATUS FOR AN ULTRASONIC INSPECTION SYSTEM, Ser. No. 815,050, filed on 12/31/85 by D. P. Sarr;

ULTRASONIC INSPECTION SYSTEM WITH LINEAR TRANSDUCER ARRAY, Ser. No. 815,047, filed on 12/31/85 by D. P. Sarr and F. D. Young;

ULTRASONIC INSPECTION SYSTEM WITH MULTIPLEXED MULTIPLE TRANSDUCER RECEIVER, Ser. No. 815,048, filed on 12/31/85 by D. P. Sarr;

ULTRASONIC INSTRUMENTATION FOR EXAMINATION OF VARIABLE-THICKNESS OBJECTS, Ser. No. 815,038, filed on 12/31/85 by D. P. Sarr;

AN IMPROVED ULTRASONIC TESTING APPARATUS, Ser. No. 815,163, filed on 12/31/85 by G. A. Geithman and D. P. Sarr; and MULTIDIRECTIONAL ULTRASONIC TESTING SYSTEM WITH MULTI-GATE AND MULTI-MODE CAPABILITY, Ser. No. 815,044, filed on 12/31/85 D. P. Sarr.

The disclosures of these applications are hereby incorporated by reference.

BACKGROUND OF THE INVENTION

This invention relates to a device for use in generation of ultrasonic signals. More particularly, the invention relates to a transducer employing a piezoelectric crystal for generating ultrasonic signals for use in through transmission ultrasonic (TTU) inspection.

TTU inspection procedures are widely used in nondestructive inspection applications such as inspection of laminated structural components. To undertake TTU inspection, a transducer generating an ultrasonic signal is aligned with an ultrasonic signal-receiving transducer, and a workpiece to be inspected is interposed between the transducers. Although the signal may be transmitted directly into an adjacent workpiece, a liquid coupling medium such as a stream of water is generally provided to allow passage of ultrasonic energy from the generating transducer to the workpiece and from the workpiece to the receiving transducer. A generating transducer and a receiving transducer may form a pair which act as a unit when they are aligned with each other on opposite sides of the workpiece being inspected.

TTU inspection is often conducted with an array of pairs of generating and receiving transducers arranged in a line. The array of transducer pairs with associated streams of coupling medium is passed over the workpiece being inspected so as to come into contact with all portions of the workpiece to produce an output signal which varies with the thickness of the workpiece and with the acoustic attenuation of the material forming the workpiece.

The output signal, representative of the ultrasonic signal intensity received at each point along the workpiece, may than be recorded on an X-Y display, with the brightness or density at each point on the display correlating to the intensity of the ultrasonic signal received at the corresponding point on the workpiece. Light shaded areas on the display indicate workpiece areas of lowered ultrasonic signal transmitting characteristics. If the low-intensity signal transmission is not due to extra thickness of the workpiece or to a known change in workpiece material composition, the low intensity shown on the X-Y display is probably indicative of a defect in the laminate layers or their bonding.

The inspection procedure described above requires precise alignment between the liquid coupling medium of the ultrasonic signal generating transducer and the liquid coupling medium of the ultrasonic signal receiving transducer. The streams of liquid that comprise the coupling media must contact the workpiece being inspected at points along the central axis of the transmitting and receiving transducers on opposite sides of the workpiece. For a conventional transducer generating signals at 1 MHz, the liquid streams must both contact the substrate within $\pm$ 0.10 inches of the generator/receiver central axis.

When a transducer generates signals for TTU inspection, an ultrasonic signal with a frequency of 1 MHz is often used. Such signals can transfer large amounts of ultrasonic energy into the workpiece and thus provide excellent results when testing relatively thick workpieces and workpieces constructed of material having high ultrasonic attenuation, such as honeycomb material.

When thin laminated components are inspected with a conventional 1 MHz ultrasonic signal, only limited attenuation occurs when the signal passes through a defective portion of the workpiece. This yields a low-contrast display in which a defect is often difficult to detect. Greater signal attenuation may be achieved with thin laminated workpieces for improved defect detection if the ultrasonic signal is generated at a frequency of 5 MHz. Unfortunately, the beam pattern of a 5 MHz frequency signal generated by prior art transducers is much less consistent than the beam pattern of a signal with a 1 MHz frequency generated by the same prior art transducers. The 5 MHz ultrasonic signal beam patterns of prior art transducers are such that signals of near peak amplitude are generated over only a narrow area at the center of the transducer. Outside of this small center area, or main lobe, the amplitude of the generated signal fluctuates irregularly.

Pairs of prior art transducers operating at 5 MHz must be positioned such that streams of coupling media are aligned to within $\pm$ 0.03 inches. However, the force of gravity on such streams makes such alignment extremely difficult, and restricts the ability to generate accurate TTU data for detecting bonding defects in a thin laminated workpiece.

If the higher ultrasonic signal frequency is not used, the maximum signal strength is consistent over a greater area. However, bonding defects in thin laminates cannot be readily detected because poorly bonded areas do not significantly attenuate a 1 MHz ultrasonic signal. It is therefore an object of the present invention to provide an ultrasonic transducer whose signal is substantially attenuated by defects in a thin workpiece and to shape the beam intensity profile of, or apodize, the transducer to permit less critical alignment of coupling media. It is a further object of the invention to provide a transducer suitable for use with workpieces having a wider range of thickness and material composition.

SUMMARY OF THE INVENTION

In accordance with the principles of the present invention there is provided an ultrasonic transducer that generates an apodized beam of ultrasonic energy. The transducer comprises a housing with a means for generating an ultrasonic signal. An ultrasonic signal attenuating means is mounted on the ultrasonic signal generating means. The attenuating means attenuates the ultrasonic signal at the periphery of the generating means by a greater amount than it attenuates the ultrasonic signal at the center of the generating means. Preferably, the attenuating means comprises a layer of attenuation material which is thicker at the periphery of the ultrasonic signal generating means than it is at the center. It is further preferred that the ultrasonic generating means comprise a piezoelectric crystal which generates ultrasonic signals upon being energized by an electrical signal.

The accompanying drawings, which are incorporated in and constitute a part of this specification, illustrate the presently preferred embodiment of the invention and, together with the description, serve to explain the principles of the invention.

DESCRIPTION OF THE PREFERRED EMBODIMENT

Reference now will be made in detail to the present preferred embodiment of the invention, an example of which is illustrated in the accompanying drawings.

Figure 1:
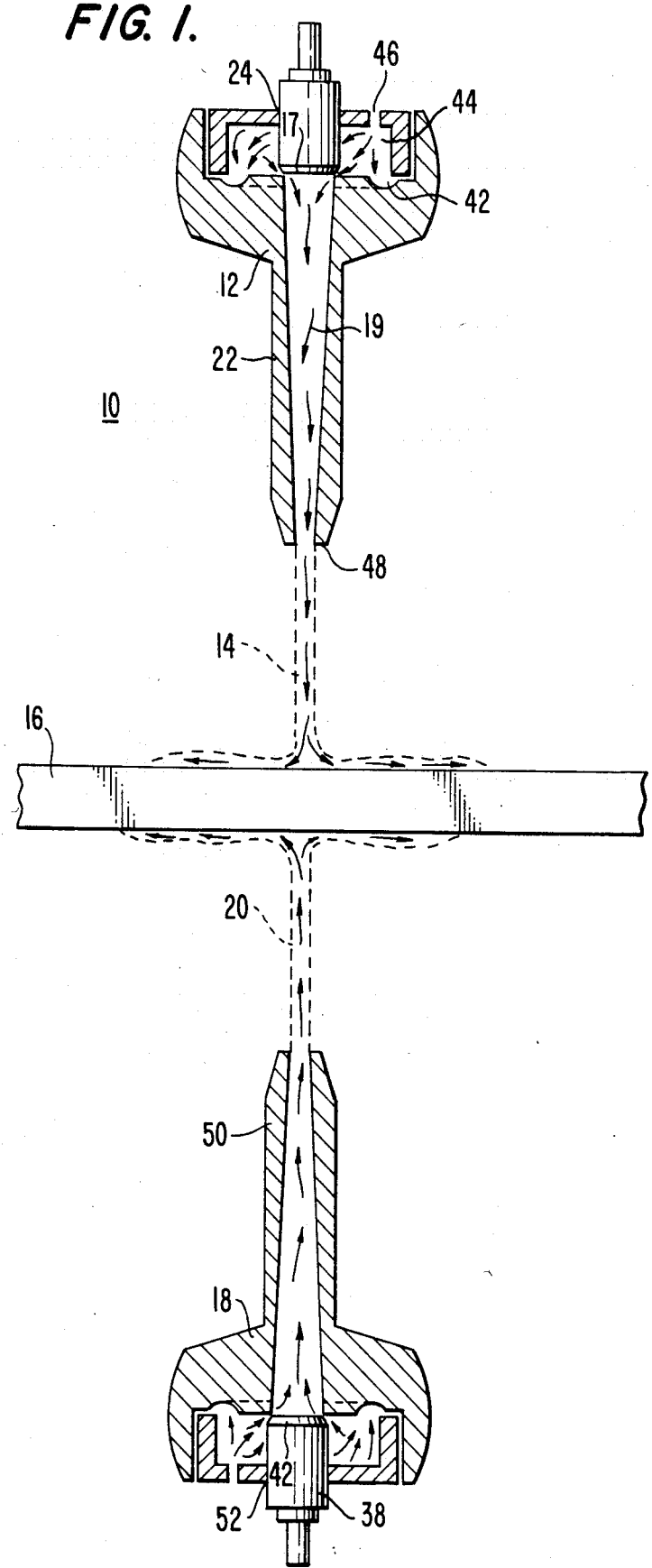
FIG. 1 shows a cross-sectional view of a TTU inspection apparatus employing ultrasonic transducers to inspect a workpiece.

Referring now to the drawings in which like reference characters refer to corresponding elements, a system 10 for TTU inspection is shown in FIG. 1. In system 10 shown, ultrasonic signals are transmitted from an ultrasonic signal sending apparatus 12 through a jet 14 of liquid such as water to a workpiece 16 that is being inspected. Ultrasonic signals that pass through workpiece 16 are detected and converted to an electrical output signal by an ultrasonic signal receiving apparatus 18 after the signals have passed through another jet 20 of liquid extending from receiving apparatus 18 to workpiece 16. The intensity of the ultrasonic signals received by the ultrasonic receiving apparatus 18 varies with the thickness of workpiece 16 and with the acoustic impedance of the material forming workpiece 16.

Figure 2:
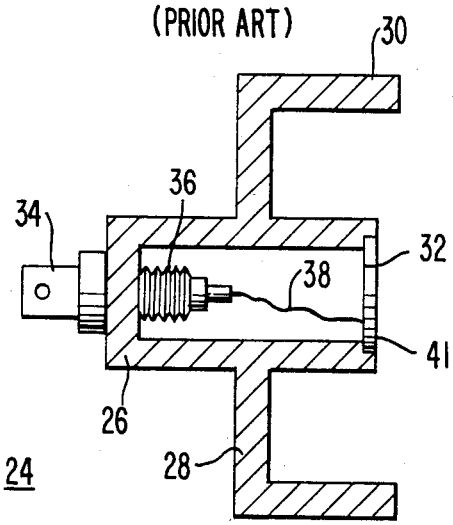
FIG. 2 is a cross-sectional view of an ultrasonic transducer according to the prior art.

Ultrasonic signal sending apparatus 12 includes a nozzle 22 and a transducer 24. A transducer 24 constructed according to the prior art is shown in FIG. 2. As can be seen therein, transducer 24 includes a hollow stainless steel housing 26 having an integrally formed flange 28 and peripheral lip 30. A piezoelectric crystal element 32 such as a crystal of lead zirconate titanate material known in the art as PZT4 having a planar front surface 41 is mounted at one end of housing 26. A connector 34 including a feed-through insulator 36 is connected to element 32 by a wire 38. Transducer 24 is mounted in nozzle 22 such that peripheral lip 30 fits into a hollow portion 42 in the base of nozzle 22. Water 44 is pumped through a hole 46 in transducer 24 and out through a tip 48 of nozzle 22 to form jet 14.

Transducer 24, when supplied with an electrical input signal, generates an ultrasonic signal which travels through jet 14 to workpiece 16. Ultrasonic signals which pass through workpiece 16 are transmitted through jet 20 and a nozzle 50 of ultrasonic receiving apparatus 18 to an ultrasonic signal receiving transducer 52. When the received ultrasonic signals contact ultrasonic signal receiving transducer 52, the ultrasonic signals are transformed into electrical signals whose intensity is proportional to the intensity of the received ultrasonic signals. These electrical signals are supplied from receiving transducer 52 through appropriate circuitry (not shown) to an output device such as a CRT or printer in which the CRT brightness or printing density (respectively) is proportional to the intensity of the electric signals generated by the ultrasonic receiving transducer 52. TTU inspection requires alignment between the ultrasonic transmitting apparatus and the ultrasonic receiving apparatus such that the respective liquid jets 14 and 20 contact the workpiece 16 being inspected at points along the central axis of transmitting and receiving transducers 24 and 52 on opposite sides of the workpiece 16. Such system provides satisfactory inspection of many types of workpieces, including workpieces made of honeycomb and moderate-thickness laminates.

When a thin laminated workpiece 16 is the subject of TTU inspection, it is desirable, as discussed above, to employ ultrasonic signals with a frequency of 5 MHz. Such signals are significantly attenuated when they pass through portions of the workpiece 16 when the workpiece laminates are poorly bonded, thus providing a high-contrast display in which a defect is more easily detected. However, problems can occur when the beam of a 5 MHz signal is generated by a transducer 24 according to the prior art.

Figure 3:
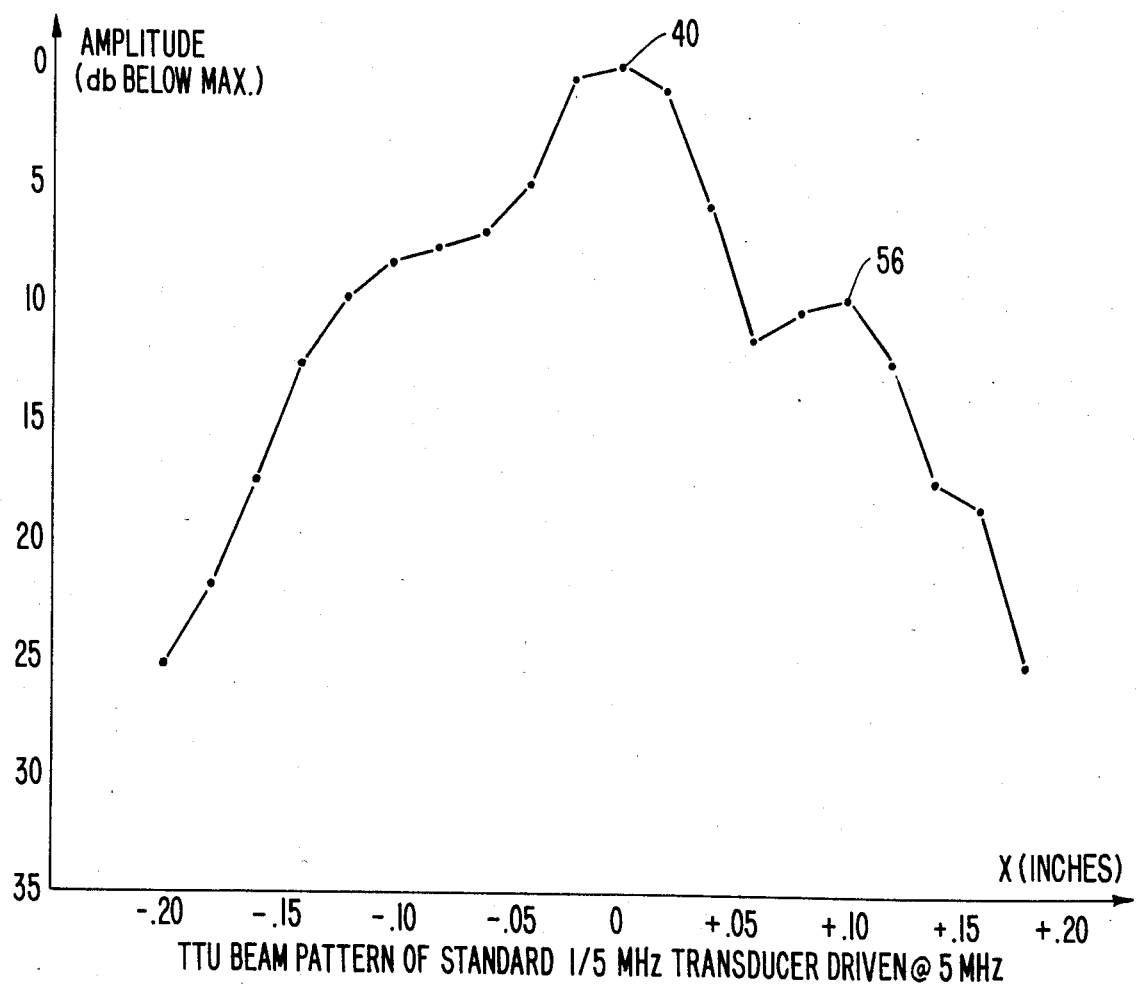
FIG. 3 is a plot of relative ultrasonic signal amplitude as a function of distance from the center of a prior art ultrasonic signal-generating transducer when the transducer operating frequency is 5 MHz.

In FIG. 3, a graph shows that the amplitude of the ultrasonic signal from a prior art transducer driven at a 5 MHz frequency is within three decibels of peak amplitude 40 over only about 0.059 inch of a 0.25 inch diameter water stream. The graph also illustrates the uneven 5 MHz beam pattern of prior art transducers exemplified by a side lobe 56. Such beam patterns require alignment between the ultrasonic signal generating and receiving apparatus 12 and 18 to a precision which is not consistently achievable.

Figure 4:
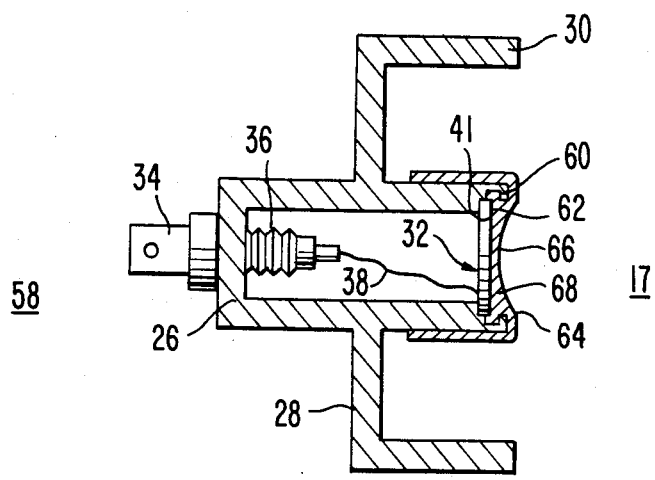
FIG. 4 is a cross-sectional view of an ultrasonic signal generating transducer according to the preferred embodiment.
Figure 5:
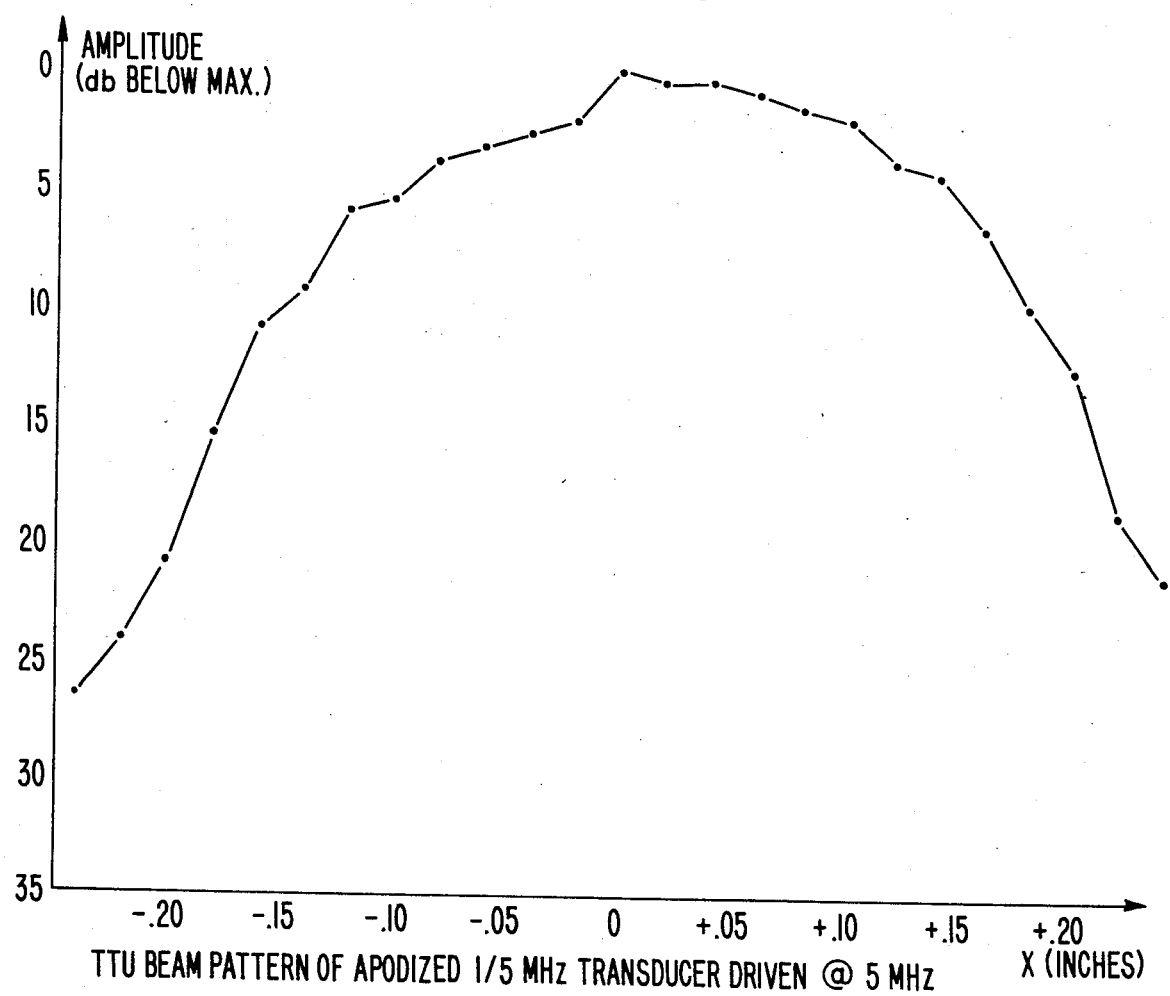
FIG. 5 is a plot of relative ultrasonic signal amplitude as a function of distance from the center of an ultrasonic signal generating transducer according to the preferred embodiment when the transducer operating frequency is 5 MHz.

The beam configuration of a 5 MHz ultrasonic signal transducer constructed according to the principles of the present invention is apodized, or intensity-shaped, to yield the more consistent beam pattern illustrated by the graph in FIG. 5. An embodiment of the present inventions is shown in FIG. 4, in which elements identical in function to elements of prior art transducers are indicated by identical reference characters.

According to the present invention, an ultrasonic transducer 58 is provided, having a housing 26 and a means mounted within housing 26 for generating an ultrasonic signal, the generating means having a first surface. As embodied herein, the means for generating the ultrasonic signal comprises piezoelectric crystal element 32 having a diameter of 0.75 inches and having a planar front surface 41. When piezoelectric crystal element 32 is energized via the electrical connector 34, piezoelectric crystal element 32 generates an ultrasonic signal. Housing 26 is surrounded by flange 28 with peripheral lip 30, which fits within the hollow portion 42 in the base of nozzle 22.

According to the invention, means are mounted upon the first surface for attenuating the ultrasonic signal. The attenuating means attenuate the ultrasonic signal at the periphery of the first surface by a greater amount than the attenuation of the ultrasonic signal by the attenuating means at the center of the first surface. As embodied herein, the attenuating means comprises a layer 60 of attenuation material mounted upon surface 41 of piezoelectric crystal element 32. Layer 60 has a flat surface 62 in contact with surface 41 of element 32 and is thicker at the periphery 64 of the piezoelectric crystal element 32 than it is at the center 66 of element 32. Layer 60 is thus provided with a concave surface 68 opposite surface 41 and facing away from the piezoelectric crystal element 32. As embodied herein, concave surface 68 may be a spherical surface with a radius of 1.125 inches and having a thickness of 0.018 inches at the center. Thus, the thickness of layer 60 at the center of surface 41 is equal to one-quarter wavelength at 1 MHz, thereby enhancing the 1 MHz efficiency of transducer 58. It is believed that a Gaussian configuration for surface 68 may yield optimum apodization of transducer 58. However, a spherical configuration can be efficiently manufactured and has proven to yield excellent results.

In the preferred embodiment, layer 60 is formed of a metal powder-epoxy resin consisting of a mixture of 50 parts by weight of epoxy resin, 100 parts by weight of tungsten powder, and 7 parts by weight of hardener. The epoxy resin may be HySol type R9-2039 and the hardener may be Hysol type HD-3485. With this composition, layer 60 has an acoustic impedance of about $7 \times 10^6$ Kg/m$^2$-S, which is the geometric mean of the acoustic impedances of PZT4 and water. The measured attenuation factor of layer 60 at 5 MHz is approximately 113 db/in.

Other types of attenuation material could, of course, be used to form layer 60, such as aluminum powder-epoxy. The most important characteristics of such material are that it exhibit a higher ultrasonic attenuation at 5 MHz than at 1 MHz and that its ultrasonic attenuation at 1 MHz be as low as possible. This permits maximum energy input to the workpiece at 1 MHz thus yielding good performance with honeycomb materials and thick workpieces, but permits apodization of the 5 MHz beam pattern to yield good performance with low attenuation materials such as thin laminates.

According to the present invention, a method for generating an apodized beam of ultrasonic energy is provided comprising the steps of generating an ultrasonic signal across a first surface 32 and transmitting the signal through a layer of attenuation material, the attenuation of the signal at the periphery of the surface being greater than the attenuation of the signal at the center of the surface. As embodied herein the attenuating step comprises the step of transmitting the ultrasonic signal through layer 60, the layer 60 being thicker at the periphery 64 of surface 41 than at the center 66 of surface 41. The ultrasonic signal generated by piezoelectric crystal element 32 is thus attenuated to a greater extent at the periphery of surface 41 than at the center.

As can be seen in FIG. 5, transducer 58 provides a significant improvement in beam pattern. The width at which beam amplitude is within 3 db of maximum beam amplitude increased from 0.059 inches to 0.160 inches. Use of transducer 58 at 5 MHz thus results in a significant reduction in the problem of aligning jets 14 and 20. Although transducer sensitivity was reduced by about 5 db compared to prior art transducers at 5 MHz, such reduction is acceptable since 5 MHz signals are only generated for use on thin laminates in which large amplitude signals are not required. Moreover, use of transducer 58 at 1 MHz results in no significant change in amplitude or beam pattern over prior art transducers. Thus transducer 58 may be readily used in both 5 MHz and 1 MHz applications and is thus adapted for use with workpieces having a wider range of thickness and composition than prior art transducers.

The ultrasonic transducer illustrated in FIG. 4 includes housing 26 with piezoelectric crystal element 32 that generates an ultrasonic signal across surface 41. The ultrasonic signal is attenuated by a layer 60 with a spherical outwardly concave surface 68, the ultrasonic signal being attenuated by a greater amount by layer 60 at the periphery 64 of surface 40 than it is attenuated at the center of the piezoelectric crystal 32. It is to be understood, however, that this configuration is merely exemplary and other configurations may be employed without departing from the spirit or scope of the present invention.

It will be apparent to those skilled in the art that modifications and variations can be made in the ultrasonic transducer of this invention. The invention in its broader aspects is, therefore, not limited to the specific details, representative methods and apparatus and illustrative examples shown and described hereinabove. Thus, it is intended that all matter contained in the foregoing description or shown in the accompanying drawings shall be interpreted as illustrative and not in a limiting sense.

What is claimed is:

1. Ultrasonic testing apparatus for detecting defects in a workpiece, said apparatus comprising:
    a supply of liquid coupling medium;
    an ultrasonic sending assembly connected to said supply, said ultrasonic sending assembly being spaced away from said workpiece and including nozzle means for producing an elongated stream of liquid coupling medium directed against the workpiece for coupling ultrasonic energy into said workpiece;
    said ultrasonic sending assembly including means for generating an ultrasonic signal having a first surface, and a layer of attenuation material formed on said first surface for coupling said ultrasonic signal into said stream, said material attenuating said ultrasonic signal at the periphery of said first surface by an amount greater than the attenuation at the center of said first surface, whereby an apodized beam of ultrasonic energy is coupled to said stream;
    means for receiving ultrasonic said ultrasonic signal; and means for analyzing said received signal to detect defects in said workpiece.

2. Ultrasonic testing apparatus for detecting defects in a workpiece, said apparatus comprising:

a supply of liquid coupling medium;

an ultrasonic sending assembly connected to said supply and generating ultrasonic energy; and an ultrasonic receiving assembly connected to said supply and receiving ultrasonic energy;

said sending and receiving assemblies being spaced away from the workpiece and located on opposite sides of the workpiece, each of said assemblies including nozzle means for producing an elongated stream of liquid coupling medium directed against the workpiece, said streams of said sending and receiving assemblies being in coaxial alignment and coupling ultrasonic energy into and out of said workpiece, respectively;

said ultrasonic sending assembly including means for generating an ultrasonic signal having a first surface, and a layer of attenuation material formed on said first surface for coupling said ultrasonic signal into said stream, said material attenuating said ultrasonic signal at the periphery of said first surface by an amount greater than the attenuation at the center of said first surface, whereby an apodized beam of ultrasonic energy is coupled to said stream.

3. The ultrasonic testing apparatus of claim 2, wherein said generating means produces an ultrasonic signal selectable between first and second frequencies, said first frequency being higher than said second frequency, said layer of attenuation material exhibiting higher ultrasonic attenuation at said first frequency signal than at said second frequency signal.

4. The ultrasonic testing apparatus of claim 3, wherein said first frequency is at least twice said second frequency.

5. The ultrasonic testing apparatus of claim 4, wherein said first frequency is 5 MHz and said second frequency is 1 MHz.

6. The ultrasonic testing apparatus of claim 5, wherein said layer has an attenuation of at least 110 db/inch for said 5 MHz signal.

7. The ultrasonic testing apparatus of claim 6, wherein said layer produces no significant change in the amplitude of said 1 MHz signal.

8. The ultrasonic testing apparatus of claim 3, wherein said layer has an acoustic impedance which is less than the acoustic impedance of said generating means and greater than the acoustic impedance of said test medium.

9. The ultrasonic testing apparatus according to claim 3, wherein said transducer comprises a piezoelectric crystal generating ultrasonic signals upon energization by an electrical signal.

10. The ultrasonic testing apparatus of claim 5, wherein said 5 MHz signal has an amplitude within 3 db of maximum signal amplitude over a width of at least 50% of the width of said stream of liquid coupling medium.

11. The ultrasonic testing apparatus of claim 8, wherein said layer is thicker at the periphery of said first surface than at the center of said first surface.

12. The ultrasonic testing apparatus of claim 11, wherein said layer comprises a metal powder-apoxy.

13. The ultrasonic testing apparatus according to claim 12, wherein said layer comprises tungsten-epoxy.

14. The ultrasonic transducer according to claim 13, wherein said layer consists essentially of a mixture of 30 parts by weight of epoxy resin, one hundred parts by weight of tungsten powder, and seven parts by weight of hardener.

15. A method for ultrasonically detecting defects in a workpiece, comprising the steps of:

generating an ultrasonic signal across a first surface;

transmitting said signal through a layer of attenuation material, the attenuation of said signal at the periphery of said first surface being greater than the attenuation of said signal at the center of said first surface so as to apodize said signal;

coupling said transmitted signal to a first elongated stream of liquid coupling medium directed against the workpieoce so as to apply said signal to the workpiece;

producing a second elongated stream of liquid coupling medium from an ultrasonic receiving assembly directed against the opposite side of the workpiece, said second stream being coaxially aligned with said first stream for transmitting said apodized signal transmitted through said workpiece;

receiving said signal on a second surface of said ultrasonic receiving assembly through said second stream of liquid coupling medium;

extracting said signal from said second stream; and analyzing said extracted signal to detect defects.

16. An ultrasonic transducer for transmitting an ultrasonic signal into an adjacent medium, comprising:

a housing;

means mounted within said housing for generating an ultrasonic signal, said means having a first surface; and a layer of attenuation material formed on said first surface, said layer having an acoustic impedance which is equal to the geometric means of the acoustic impedances of said generating means and said adjacent medium.

17. A method for generating an apodized beam of ultrasonic energy to be transmitted an adjacent medium, comprising the steps of:

generating an ultrasonic signal across a first surface; and transmitting said signal through a layer of attenuation material having an acoustic impedance equal to the geometric mean of the acoustic impedance of the material generating the signal and the acoustic impedance of the adjacent medium, the attenuation of said signal at the periphery of said first surface being greater than the attenuation of said signal at the center of said first surface.

* * * * *